(12) United States Patent
Kuiken et al.

(10) Patent No.: US 8,828,093 B1
(45) Date of Patent: Sep. 9, 2014

(54) IDENTIFICATION AND IMPLEMENTATION OF LOCOMOTION MODES USING SURFACE ELECTROMYOGRAPHY

(75) Inventors: Todd Kuiken, Oak Park, IL (US); He Huang, Warwick, RI (US)

(73) Assignee: Rehabilitation Institute of Chicago, Chicago, IL (US)

( * ) Notice: Subject to any disclaimer, the term of this patent is extended or adjusted under 35 U.S.C. 154(b) by 676 days.

(21) Appl. No.: 12/419,521

(22) Filed: Apr. 7, 2009

Related U.S. Application Data

(60) Provisional application No. 61/045,130, filed on Apr. 15, 2008.

(51) Int. Cl.
A61F 2/70 (2006.01)

(52) U.S. Cl.
USPC .......................................................... 623/25

(58) Field of Classification Search
CPC ...................................................... A61F 2/72
USPC ........................................................... 623/25
See application file for complete search history.

(56) References Cited

U.S. PATENT DOCUMENTS

| | | | | | |
|---|---|---|---|---|---|
| 4,030,141 | A | * | 6/1977 | Graupe | 623/25 |
| 4,209,860 | A | * | 7/1980 | Graupe | 623/25 |
| 5,875,108 | A | * | 2/1999 | Hoffberg et al. | 700/17 |
| 6,673,117 | B1 | * | 1/2004 | Soss et al. | 623/24 |
| 7,029,500 | B2 | * | 4/2006 | Martin | 623/50 |
| 7,147,667 | B2 | * | 12/2006 | Bedard | 623/24 |
| 7,150,762 | B2 | * | 12/2006 | Caspers | 623/33 |
| 7,209,788 | B2 | * | 4/2007 | Nicolelis et al. | 607/48 |
| 7,393,364 | B2 | * | 7/2008 | Martin | 623/50 |
| 7,398,255 | B2 | * | 7/2008 | Lauer et al. | 706/8 |
| 7,485,152 | B2 | | 2/2009 | Haynes et al. | |
| 2004/0049290 | A1 | * | 3/2004 | Bedard | 623/24 |
| 2004/0054423 | A1 | * | 3/2004 | Martin | 623/25 |
| 2004/0093093 | A1 | * | 5/2004 | Andrews | 623/25 |
| 2005/0192677 | A1 | * | 9/2005 | Ragnarsdottir et al. | 623/24 |
| 2005/0197717 | A1 | * | 9/2005 | Ragnarsdottir et al. | 623/24 |
| 2005/0228515 | A1 | * | 10/2005 | Musallam et al. | 700/83 |
| 2006/0015470 | A1 | * | 1/2006 | Lauer et al. | 706/8 |
| 2006/0122710 | A1 | * | 6/2006 | Bedard | 623/24 |
| 2006/0155385 | A1 | * | 7/2006 | Martin | 623/24 |
| 2006/0173552 | A1 | * | 8/2006 | Roy | 623/24 |
| 2006/0224246 | A1 | * | 10/2006 | Clausen et al. | 623/24 |
| 2006/0224247 | A1 | * | 10/2006 | Clausen et al. | 623/24 |

(Continued)

OTHER PUBLICATIONS

Peeraer et al., "Development of EMG-based mode and intent recognition algorithms for a computer-controlled above-knee prosthesis," *J. Biomed. Eng.*, vol. 12, pp. 178-182, May 1990.

(Continued)

*Primary Examiner* — David Isabella
*Assistant Examiner* — Jacqueline Woznicki
(74) *Attorney, Agent, or Firm* — Drinker Biddle & Reath LLP

(57) ABSTRACT

Apparatus and methods are provided for determining a locomotion mode that can be provided to a controller of a lower prosthesis limb in order to accurately control the prosthesis. One or more prosthesis sensors are provided that break a gait cycle down into a plurality of gait phases. EMG sensors provide signals to a processor that directs them to a gait phase specific classifier that is used to determine a particular locomotion mode for the wearer. With the locomotion mode accurately known, the prosthetic device can be accurately controlled.

22 Claims, 8 Drawing Sheets

(56) References Cited

U.S. PATENT DOCUMENTS

| | | | |
|---|---|---|---|
| 2007/0046486 A1* | 3/2007 | Donoghue et al. | 340/825.19 |
| 2007/0050045 A1* | 3/2007 | Clausen et al. | 623/24 |
| 2007/0050047 A1* | 3/2007 | Ragnarsdottlr et al. | 623/24 |
| 2007/0156252 A1* | 7/2007 | Jonsson et al. | 623/24 |
| 2007/0225611 A1* | 9/2007 | Kumar et al. | 600/523 |
| 2008/0228287 A1 | 9/2008 | Ninomiya | |

OTHER PUBLICATIONS

Jin et al., "Terrain Identification for Prosthetic Knees Based on Electromyographic Signal Features," *Tsinghua Science and Technology*, vol. 11(1), pp. 74-79, Feb. 2006.

Kuiken et al., "Targeted reinnervation for enhanced prosthetic arm function in a woman with a proximal amputation: a case study," *Lancet*, vol. 369, pp. 371-380, Feb. 3, 2007.

Kuiken et al., "The use of targeted muscle reinnervation for improved myoelectric prosthesis control in a bilateral shoulder disarticulation amputee," *Prosthet. Orthot. Int.*, vol. 28, pp. 245-253, 2004.

Zhou et al., "Decoding a New Neural-Machine Interface for Control of Artificial Limbs," *J. Neurophysiol*, vol. 98, pp. 2974-2982, Aug. 29, 2007.

Huang et al., "An Analysis of EMG Electrode Configuration for Targeted Muscle Reinnervation Based Neural Machine Interface," *IEEE Transactions on Neural Systems and Rehabilitation Engineering*, vol. 16 (1), pp. 37-45, Feb. 2008.

Englehart et al., "A Robust, Real-Time Control Scheme for Multifunction Myoelectric Control," *IEEE Transactions on Biomedical Engineering*, vol. 50 (7), pp. 848-854, Jul. 2003.

Englehart et al., "Classification of the myoelectric signal using time-frequency based representations," *Medical Engineering & Physics*, vol. 21, pp. 431-438, 1999.

Hargrove et al., "A Comparison of Surface and Internally Measured Myoelectric Signals for use in Prosthetic Control," *IEEE Transactions on Biomedical Engineering*, vol. 54, pp. 847-853, 2007.

Huang et al., "A Gaussian Mixture Model Based Classification Scheme for Myoelectric Control of Powered Upper Limb Prostheses," *IEEE Transactions on Biomedical Engineering*, vol. 52, pp. 1801-1811, 2005.

Hudgins et al., "A new strategy for multifunction myoelectric control," *IEEE Transactions on Biomedical Engineering*, vol. 40, pp. 82-94, 1993.

Hall et al., "An Introduction to Multisensor Data Fusion," *Proceedings of the IEEE*, vol. 85 (1), pp. 6-23, Jan. 1997.

Huang et al., "Recent developments in biofeedback for neuromotor rehabilitation," *Journal of NeuroEngineering and Rehabilitation*, vol. 3, pp. 11-22, Jun. 21, 2006.

Delagi et al., "Anatomic Guide for the Electromyographer—The Limbs," $2^{nd}$ Edition, Charles C. Thomas—Publisher, Springfield, Illinois, pp. 122-123, 144-147, 150-151, 156-159, 170-175, 180-183, 186-187, 192-195, 198-201 (1980).

\* cited by examiner

IDENTIFICATION AND IMPLEMENTATION OF LOCOMOTION MODES USING SURFACE ELECTROMYOGRAPHY

BACKGROUND

Recent designs of lower-limb prostheses for amputee patients improve stability and may also provide a decrease in energy consumption in level ground walking. In addition, advances in computerized control and powered-prosthesis design have further improved the function of artificial legs which now can assist users with versatile activities beyond level walking. However, without knowing user movement intent, current artificial limbs cannot properly select the correct control mode to adjust the joint impedance or drive powered joint motion.

Current computerized prosthetic legs allow the user to change the movement mode manually. Such voluntary prosthesis control is cumbersome and does not allow smooth task transition. Therefore, neural control of computerized, powered prosthetic legs would provide an important advance in the art.

Surface electromyographic (EMG) signals represent neuromuscular control information of the user and are readily accessible. EMG signals are one of the major neural control sources for powered upper limb prostheses, experimental motorized orthoses, and rehabilitation robots. Although myoelectric control and advanced EMG pattern recognition (PR)-based control have been used in upper-limb prostheses, no EMG-controlled lower-limb prostheses are available.

While studies have attempted to use EMG signals to identify locomotion modes for prosthetic leg control, they lack systematic experimental design and study methodology. For example, Peeraer et al. (L. Peeraer, B. Aeyels, and G. Van der Perre, "Development of EMG-based mode and intent recognition algorithms for a computer-controlled above-knee prosthesis,"*J Biomed Eng, vol.* 12, pp. 178-82, 1990) demonstrated the difference in the EMG signal envelope among level ground walking and ascending and descending a ramp and concluded that EMG signals from hip muscles might be used to classify these locomotion modes. However, no method or apparatus for neural control of computerized, powered prosthetic legs was described or suggested.

Jin et al. (D. Jin, J. Yang, R. Zhang, R. Wang, and J. Zhang, "Terrain Identification for Prosthetic Knees Based on Electromyographic Signal Features," *Tsinghua Science and Technologys, vol.* 11, pp. 74-9, 2006) developed an algorithm for terrain identification during walking. The features were extracted from EMG signals from a complete stride cycle. Using such features, the algorithm only made one decision per stride cycle, resulting in a full stride cycle time delay (generally over 1 second) in real-time. In practical application, this is inadequate for safe prosthetic control. A strategy for effective neural control of computerized, powered prosthetic legs must include means for generating timely updates of the user's lower-limb movement modes.

One of the challenges in using EMG signals from leg muscles to classify user's movement modes in a timely manner is that the recorded EMG signals are time-varying. The features of gait EMG signals generally show large variation within the same task mode (class), which might result in overlaps of features among classes and therefore low accuracy for pattern recognition. Work in upper-limb prosthesis control, however, has suggested EMG signals, though time-varying, have a relatively small change in signal content within the short time duration of 200 ms.

Another challenge is that the accuracy of EMG PR might be inadequate for robust prosthesis control in patients with high-level amputations because insufficient neural content is available in EMG signals from only the residual limb. However, the neural control information for the amputated limb remains in the patient's residual nerves.

To allow access to these neural control commands via EMG signals, a novel neural-machine interface (NMI) technology called targeted muscle reinnervation (TMR) has been developed and successfully applied on patients with transhumeral or higher amputations for improved myoelectric artificial arm control. (See T. A. Kuiken, L. A. Miller, R. D. Lipschutz, B. A. Lock, K. Stubblefield, P. D. Marasco, P. Zhou, and G. A. Dumanian, "Targeted reinnervation for enhanced prosthetic arm function in a woman with a proximal amputation: a case study," *Lancet, vol.* 369, pp. 371-80, 2007; and T. A. Kuiken, G. A. Dumanian, R. D. Lipschutz, L. A. Miller, and K. A. Stubblefield, "The use of targeted muscle reinnervation for improved myoelectric prosthesis control in a bilateral shoulder disarticulation amputee," *Prosthet Orthot Int, vol.* 28, pp. 245-53, 2004, which are incorporated by reference for their description of TMR).

In TMR surgery, the residual nerves are transferred to alternative residual muscles that are no longer biomechanically functional. After successful motor reinnervation, the voluntary neural control signals propagate along the efferent nerves and activate the residual muscles. The resultant EMG signals, containing neural control information for a missing arm and hand, can control an artificial elbow, wrist, and even thumb/fingers via an EMG PR method. (See P. Zhou, M. M. Lowery, K. B. Englehart, H. Huang, G. Li, L. Hargrove, J. P. Dewald, and T. A. Kuiken, "Decoding a New Neural-Machine Interface for Control of Artificial Limbs," *J Neurophysiol,* 2007; and H. Huang, P. Zhou, G. Li, and T. A. Kuiken, "An analysis of EMG electrode configuration for targeted muscle reinnervation based neural machine interface," *IEEE Trans Neural Syst Rehabil Eng, vol.* 16, pp. 37-45, 2008, which are incorporated by reference).

If TMR could be used for leg prosthesis control, it could provide control information for the lower leg and foot in the form of EMG signals from reinnervated muscle. However, much must be done to implement a TMR based system for neural control of computerized, powered prosthetic legs before clinical applications can be implemented.

SUMMARY

A new EMG PR-based neural-machine interface for user locomotion mode recognition is provided. A variety of mobility tasks are identified by non-stationary EMG signals recorded from leg muscles. A new phase-dependent EMG pattern recognition strategy is provided. EMG data recorded from able-bodied subjects and a subject with a long transfemoral (TF) amputation is used to demonstrate the potential of the designed EMG PR algorithm for neural control of artificial legs including task identification accuracy.

This invention is therefore directed to the use of surface electromyography (EMG) combined with pattern recognition (PR) to identify user locomotion modes. A new EMG PR strategy that is phase-dependent is used for classifying the user's locomotion modes. A phase-dependent EMG PR algorithm, such as a Linear Discriminant Analysis (LDA)-based classifier (or others) may be used for identifying locomotion modes, and for the design of neural-controlled prosthetic legs. The EMG PR design permits many activities of daily living to be identified by the classifier, and makes the accuracy of recognizing the user's movement mode acceptable for safe and robust prosthetic control.

Accordingly, a lower-limb prosthesis operating assembly is provided, comprising: one or more prosthesis sensors, each one for measuring one or more prosthesis characteristics and for providing characteristic values at an output; a processor comprising one or more inputs connected to outputs of the prosthesis sensors that receives the prosthesis characteristic values; a gait phase algorithm for determining gait phase information relating to a specific phase of a gait cycle based on the prosthesis characteristic values; and a memory for storing the determined gait phase information; a plurality of electromyographic (EMG) sensors affixed to or connected to a portion of the prosthesis. The processor further comprises one or more inputs that receives digitized EMG sensor signals; a locomotion mode algorithm for determining a locomotion mode based on the EMG sensor signals and the gait phase information; and a memory for storing the determined locomotion mode. Finally, the prosthesis operating assembly further comprises an output that presents the determined locomotion mode at the determined gait phase to a prosthesis controller input.

Additionally, a method is provided for determining locomotion mode information that is given to a controller of a lower-limb prosthesis comprising affixing a plurality of prosthesis sensors to the prosthesis; affixing or connecting a plurality of electromyographic (EMG) sensors to the prosthesis; determining, using a gait phase algorithm running on a processor, a phase of a gait based on an output of the prosthesis sensors; storing in a memory the determined gait phase information; measuring signals from the plurality of EMG sensors and converting them from analog to digital signals; inputting the digital signals from the EMG sensors and the stored determined gait phase information to a processor running a locomotion mode algorithm; determining a locomotion mode based on the gait phase information and the signals from the EMG sensors; and providing the locomotion mode at the determined gait phase to an input of a controller of the lower-limb prosthesis.

BRIEF DESCRIPTION OF THE DRAWINGS

The invention is described in more detail below with reference to various embodiments of the invention illustrated in the drawings, in which.

DETAILED DESCRIPTION OF THE EMBODIMENTS

A description of various illustrative embodiments of the invention follows.

Figures 1, 2:
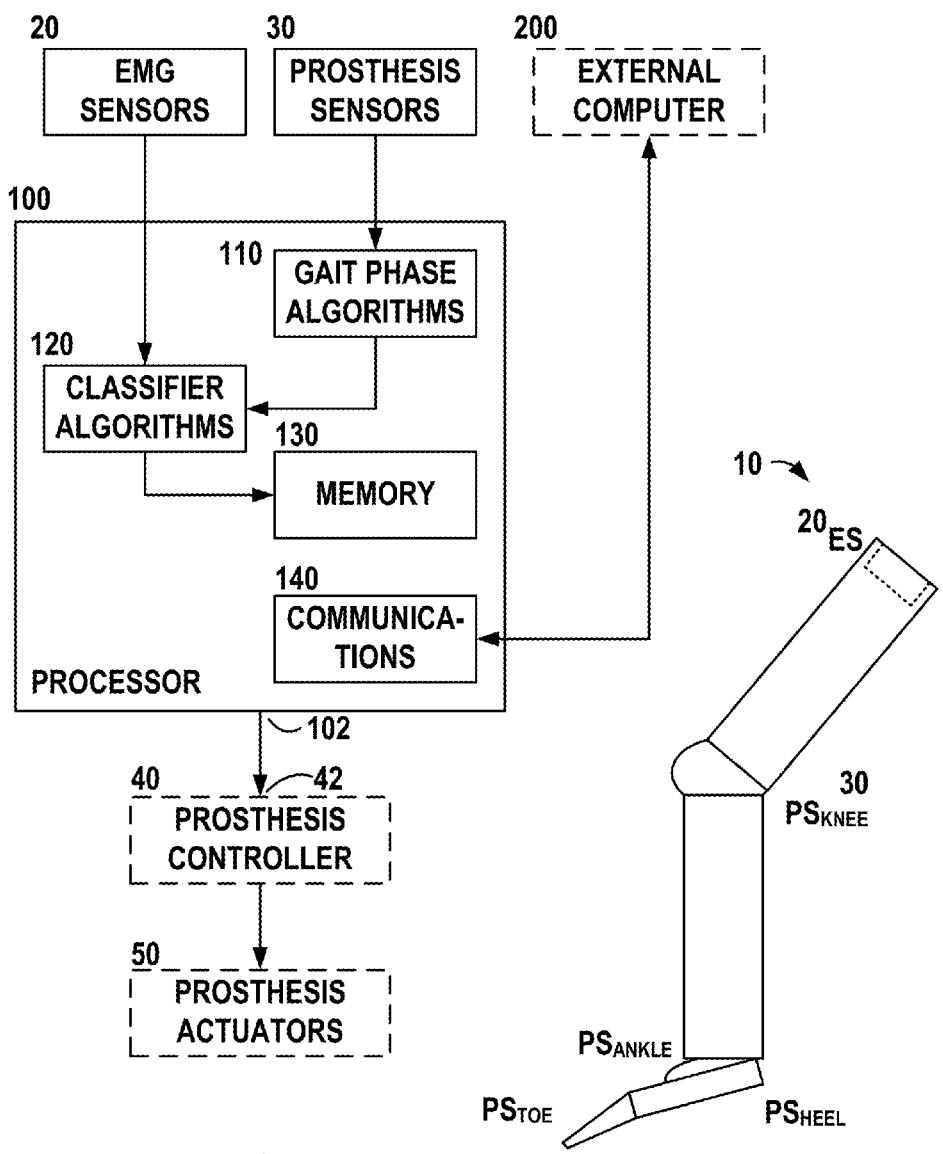
FIG. 1 is a pictorial diagram illustrating a basic lower-limb prosthesis.
FIG. 2 is a block diagram illustrating the primary components of the lower-limb prosthesis.

FIG. 1 illustrates a very basic lower-limb prosthesis 10 comprising the major sectional components along with exemplary sensors 20, 30. The sensors are basically categorized as electromyographic (EMG) sensors ES (20) that measure aspects of the user, and prosthesis sensors PS (30) that measure aspects of the prosthesis 10 itself.

The EMG sensors 20 can be implemented as polarizable electrodes, such as stainless steel domes, embedded into the sockets or the liner of the prosthesis 10, although sensors 20 could also be located on muscles or muscle groups that are not directly above or below an area that is directly contacted by a portion of the prosthesis 10—in such a case, wires or wireless technologies could be used to communicate information from the sensors 20. The EMG sensors 20 can be placed as targeted (electrodes placed at specific muscles), untargeted (electrodes placed over groups of more than one muscle), or in a combination of targeted and untargeted in order to yield high classification results. The monitored muscles could include:

| | |
|---|---|
| the gluteus maximus | (GMA) |
| gluteus medius | (GME) |
| sartorius | (SAR) |
| rectus femoris | (RF) |
| vastus lateralis | (VL) |
| vastus medialis | (VM) |
| gracilis | (GRA) |
| biceps femoris long head | (BFL) |
| semitendinosus | (SEM) |
| biceps femoris short head | (BFS) |
| tibialis anterior | (TA) |
| peroneus longus | (PL) |
| gastrocnemius lateral head | (GASL) |
| gastrocnemius medial head | (GASM) |
| soleus | (SOL) |
| extensor digitorum brevis | (EDB). |

The prosthesis sensors 30 measure attributes of the prosthesis at various locations. FIG. 1 illustrates a knee sensor $PS_{KNEE}$, ankle sensor $PS_{ANKLE}$, toe sensor $PS_{TOE}$, and heel sensor $PS_{HEEL}$. Other prosthesis sensors could be located at various additional positions anywhere on the prosthesis, and could be used to measure position, angle, velocity, acceleration, torque, linear vector forces, and other relevant attributes.

FIG. 2 is a block diagram illustrating the various components of the prosthetic device 10 and external connections. Both the EMG sensors 20 and the prosthesis sensors 30 interface with a processor 100 of the prosthetic device 10 that process signals received in a manner described in more detail below. The processor 100 comprises an output 102 that is communicates with a prosthesis controller 40, the output 102 being connected to an input 42 of the controller 40. The controller provides control signals to prosthesis actuators 50 that control movements of various components of the prosthetic device 10 itself.

The processor 100 is programmed to execute various algorithms, including gait phase algorithms 110 and classifier algorithms 120 that are stored in program memory of the processor 100. The prosthesis sensors 30 provide sensor information to the gait phase algorithms 110, which determine a current gait phase based on attribute values measured by the prosthesis sensors 30. The EMG sensors 20 provide EMG information to the classifier algorithms 120 that are used to help determine the locomotion mode for a particular gait phase.

The processor also has a memory 130 for storing data associated with the various algorithms. The processor has a communications module 140 for communicating with external entities, such as a computer 200 that can be used for communicating algorithm 110, 120 updates, training data, log information, etc. The communications module 140 is preferably able to communicate wirelessly, e.g., via Blue-Tooth™ or WiFi™, or any other known wireless protocol, but can also communicate in a wired manner (such as via USB™) if desired. The communication module 140 can be particularly helpful in adjusting the pattern recognition algorithms used by the classifier 120 (and possibly even the gait phase algorithms 110). Although prosthesis will initially attempt to mimic a gait profile that is based on a pre-existing normative database of able-bodied walkers, the pattern recognition algorithms can learn what each patient's EMG signals look like, and with the intuitive interface, the pattern recognition algorithm can be adjusted for each person. Data from each user can be stored in the memory 130 and extracted via the communications module 140 to further refine the algorithms for the particular user, but also the normative data that is used for subsequent devices 10.

Figure 3:
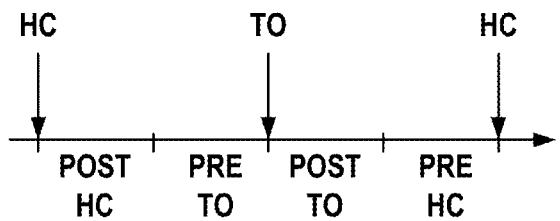
FIG. 3 is a timing diagram illustrating possible prosthesis events and gait phase delineation.

FIG. 3 illustrates an exemplary gait phase broken down into four distinct phases based on two measurable or estimatable events. In this exemplary embodiment, the two measurable events are utilized: the heel contact HC and the toe off TO. One way to determine these would be to utilize a heel sensor $PS_{HEEL}$ and a toe sensor $PS_{TOE}$. Heel contact HC could be determined by a measured sharply increasing force change on the heel sensor $PS_{HEEL}$. Similarly, toe off TO could be determined by a measured relatively sharply decreasing force change on the toe sensor $PS_{TO}$. Force profile matching could be utilized to more accurately determine these events.

Additionally, load cells having different degree-of-freedom (DOF) measurements could be used as well. For example, with a three DOF load cell, a change to a vertical force of zero could be used to determine that the prosthesis had left the ground and the toe off TO had just occurred. Alternatively, when the vertical force changes from zero to a non-zero value, it can be inferred that the heel contact HC has occurred.

Other sensor attributes (forces, torques, accelerations, positions) could be used in making the determination as to the gait phase, and the invention is not limited to only using heel contact HC and toe off TO events to delineate the gait phase. Furthermore, any number of measurable events could be used to make the gait phase determination.

As can be seen in FIG. 3, four phases have been identified: post HC, pre TO, post TO, and pre HC. Since the gait phase algorithms 110 cannot predict the future, the determination of the pre TO and pre HC phase beginnings would have to be estimated and based on timing related to a gait cycle prior to the current gait cycle. Note that these phases do not have to be evenly divided. Measurements can be made during the entire phase period, or can be made over some period of time. Advantageously, it has been found that measurements provided for between about 120 ms and 200 ms in each phase resulted in good classification characteristics, even when these time periods overlapped for rapid leg motion that results in shorter gait cycles.

It should be noted, however, that the four-phase breakdown is exemplary and greater or fewer phases could be used and these could be based on other measurable or estimatable events.

The EMS sensors 20 and prosthesis sensors 30 (if analog) are preferably connected to the processor 100 via analog-to-digital (A/D) converters. Currently, twelve-bit A/D converters are used as a compromise between cost and the desired resolution to get good results. The processor 100 for implementing the gait phase 110 and classifier 120 algorithms could be an integer-based (e.g., PIC32 micro-controller) controller, or it could be a floating point processor (e.g., a TMS320F283xx™ micro-controller).

Figure 4:
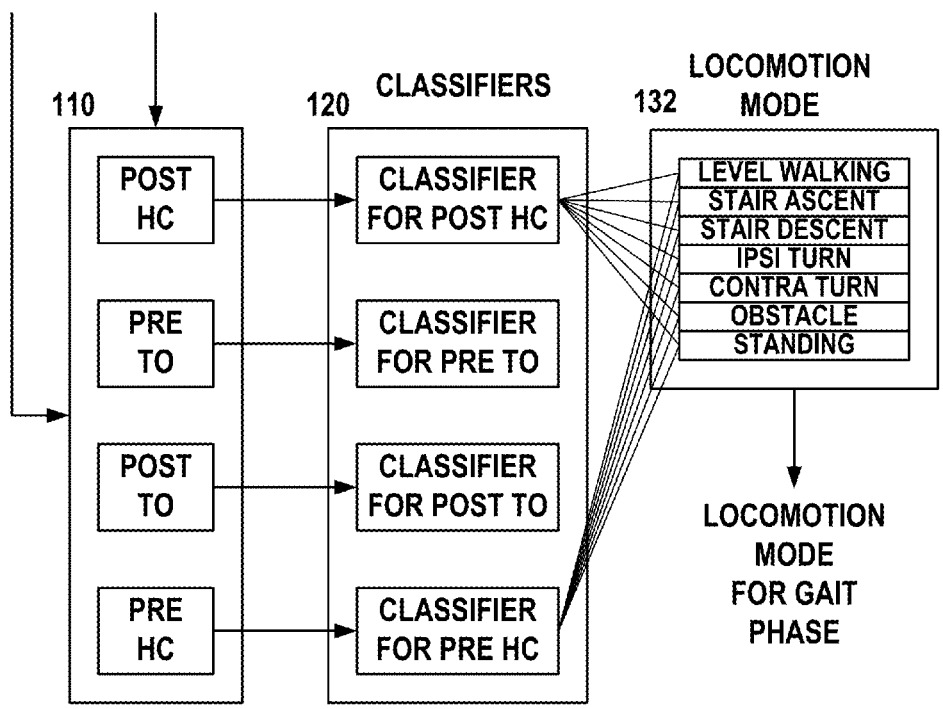
FIG. 4 is a block diagram illustrating the relationship between the sensors, classifier, and locomotion mode.

Referring to FIG. 4, the prosthesis sensor 30 outputs are provided to the gait phase algorithm 110 that determines which of the gait phases the device 10 is currently in, and directs the output of the EMS sensors 20 to the appropriate classifier 120. For example, if the gait phase is identified as being post HC, then the EMG sensor outputs are directed to the classifier for the post HC phase.

For each of the classifiers 120, a particular locomotion mode 132 can be determined based on the EMS sensor 20 outputs. Although FIG. 4 only illustrates the association of different locomotion modes for the first and last gait phase, it should be understood that this association exists for each of the gait phases.

The locomotion mode can thus be determined and stored in the memory 130 so that it can be provided and utilized for more accurate control by the actual prosthesis controller 40. The controller 40 can be used to adjust the join motion and impedances through known technologies, such as following a pre-programmed position trajectory, and others.

Experimental Observations and Results

The embodiments of the invention described herein are based on experimental research data which is presented below and provided as supporting disclosure. Thus, the following experimental configuration and data further illustrates various aspects of the invention but should not be construed as in any way limiting its scope.

The variables of the system were studied for accurate classification and timely system response. The developed PR system was tested on EMG data collected from eight able-bodied subjects and one subject with a long transfemoral (TF) amputation while they were walking on different terrains or paths. The results showed reliable classification for the seven modes tested.

For eight able-bodied subjects, the average classification error using ten electrodes located over the muscles above the knee (simulating EMG from the residual limb of a transfemoral amputee) was 12.4±5.0%, 6.0±4.7%, 7.5±5.1%, and 5.2±3.7% in four defined phases, respectively. A comparable result was also observed in a pilot study on the subject with a long TF amputation.

A. Participants and Measurements

First, four male subjects and four female subjects free from orthopedic or neurological pathologies were recruited for this study. The age of the subjects ranged from 25 to 61 (41.3±12.9 yr). The average weight of the subjects was 65.8 (±7.7) kg and the average height was 1.71 (±0.05) m. In order to extract neuromuscular control information from the lower limb, sixteen channels of surface EMG signals from muscles on one side of the hip, thigh, calf and foot were collected. The monitored muscles included:

| | |
|---|---|
| the gluteus maximus | (GMA) |
| gluteus medius | (GME) |
| sartorius | (SAR) |
| rectus femoris | (RF) |
| vastus lateralis | (VL) |
| vastus medialis | (VM) |
| gracilis | (GRA) |
| biceps femoris long head | (BFL) |
| semitendinosus | (SEM) |
| biceps femoris short head | (BFS) |
| tibialis anterior | (TA) |
| peroneus longus | (PL) |
| gastrocnemius lateral head | (GASL) |
| gastrocnemius medial head | (GASM) |
| soleus | (SOL) |
| extensor digitorum brevis | (EDB). |

The bipolar electrodes were placed over the anatomical locations described by Delagi and Perotto (See E. F. Delagi and A. Perotto, Anatomic guide for the electromyographer—the limbs, 2d ed. Springfield, Ill.: Thomas, 1980), which is incorporated herein by reference.

Since the design of the EMG-based NMI was motivated by the need for neural control of artificial legs, a 51-year-old male subject with a unilateral, long transfemoral amputation for more than 30 years was also recruited. The EMG data from his residual limb were used for evaluating the designed algorithm. The length of his residual limb measured from the greater trochanter to the amputated site was about 82% of the thigh length on the non-impaired side measured from the greater trochanter to lateral epicondyle. Two gluteal muscles (GMA and GME) and nine residual muscles in the residual thigh such as the SAR, RF, VL, VM, GRA, BFL, SEM, BFS, and adductor megnus (ADM) were monitored. The locations of EMG electrodes on the distal muscles were approximate.

For the able-bodied subjects, the active, bipolar surface EMG electrodes (MA-411 EMG pre-amplifier, Motion Lab System Inc., Baton Rouge, La.) had two circular sensor contacts (12 mm in diameter), between which was one rectangular reference contact to remove the electromagnetic environmental noise. The center-to-center separation of the two poles was 18 mm. The pre-amplifier provided analog amplification with a pass-band gain of 20 and with high and low cut-off frequencies of 20 Hz and 3,000 Hz, respectively.

For the subject with a TF amputation, the EMG electrodes (MA-411-002 EMG pre-amplifier, Motion Lab System Inc., Baton Rouge, La.), consisting of two contacts only, were mounted on an experimental socket. The electrode dimensions and the parameters of the pre-amplifier were the same as those used for able-bodied subjects. The electrodes were modified by replacing the two contacts with LTI (Liberty Technology Inc, Holliston, Mass.) electrode domes, which can penetrate the experimental socket for reliable electrode-skin contact. Before the electrode placement or the experimental socket donning, the skin was shaved and cleaned. A ground electrode was placed on the bony area of the knee for able-bodied subjects and near the anterior iliac spine for the amputee subject.

Gait events were quantified by the force-sensitive resistor-based footswitches placed under the tested foot and enhanced via the motion data of light reflective markers placed over the heel and toe. A MA-300-16 system (Motion Lab System Inc., Baton Rouge, La.) collected 16-channels of EMG data and footswitch data simultaneously but independently. The cut-off frequency of the anti-aliasing filter was 500 Hz for the 16 EMG channels and was 120 Hz for footswitch data. Both data sources were then digitally sampled at a rate of 1440 Hz. The markers' positions were captured by six motion-tracking cameras (Motion Analysis Corp., Santa Rosa, Calif.) and then sampled at 120 Hz. All the recordings were synchronized.

B. Experiment Protocol

The able-bodied subjects wore their own walking shoes, and the TF amputee subject wore his own prosthesis consisting of a Mauch® SNS knee and a 27 cm Vari-Flex® foot (Ossur, Reykjavik, Iceland). An experimental socket fitted with EMG electrodes was duplicated from his own ischial containment socket with suction suspension. In addition, a total elastic suspension (TES) belt was applied to reinforce the socket suspension. The subjects received instructions and practiced the tasks several times prior to measurement.

Seven movement modes were investigated: level ground walking, stepping over an obstacle, ascending stairs, descending stairs, ipsilateral turning, contralateral turning, and standing still. Level walking was tested on a straight walkway 9 m in length. Subjects were instructed to walk at a comfortable speed. For the task of stepping over an obstacle, subjects were asked to step over a box (19 cm high×30 cm wide×10 cm deep) during ambulation.

For the able-bodied subjects, the non-testing side was required to pass over the obstacle first, followed by the instrumented leg. The amputee subject was instructed to use his own preference; he chose to step over the obstacle using the amputated limb first. A three-stair staircase was used for stair ascent/descent tests. The staircase was 20 cm high, 75 cm wide, and 26 cm deep. Subjects ascended/descended stairs using a normal alternating fashion. The recruited TF amputee subject was capable of performing the stair ascent/descent with the alternating pattern when using hand railings.

In the turning tasks, the subjects were instructed to perform 90-degree turns to either the right or left during locomotion. When the turning direction was consistent with the side of tested leg, the task was called ipsilateral turning; otherwise, the task was termed contralateral turning. Previous studies indicated two turning strategies, step turn and spin turn, depending on the side of the foot used as the pivot. The turning strategy used for both the able-bodied subjects and the amputee subject in this study was the step turn that employed the contralateral limb as the pivot. Finally, EMG signals were recorded while the subjects were standing still.

In each trial, subjects performed one type of task. Each locomotion mode was repeated, and at least ten complete stride cycles of each task mode were recorded. The order of the tasks was randomly assigned. Rest periods were allowed between trials to avoid fatigue.

C. Data Analysis

1. Phase-Dependent Classifier

Conventional classifiers for upper-limb prosthesis control may not correctly identify the locomotion mode because within the same mode, the leg EMG patterns (FIG. 6) change over time. Fortunately, gait EMG, although time varying, are quasi-cyclic; the muscles' activation pattern for the same locomotion mode is similar at the same gait phase.

Figure 5:
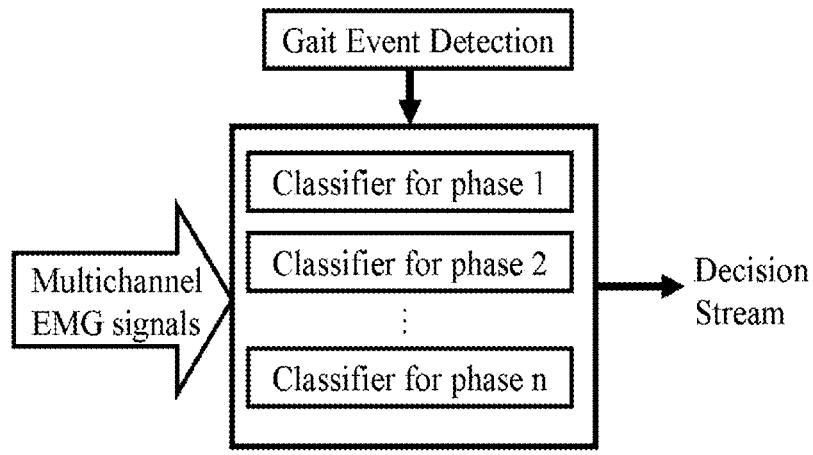
FIG. 5 is block diagram representing an architecture of a phase-dependent EMG pattern classifier in accordance with an embodiment of the present invention.

In addition, it was assumed that the pattern of gait EMG signals had small variation in a short time window and therefore designed a phase-dependent EMG pattern classifier to recognize the user's locomotion modes with a fast time response (FIG. 5). It was also hypothesized that the phase-dependent PR design could provide more reliable classification than a more conventional PR system which uses EMG signals from an entire stride.

Figure 6:
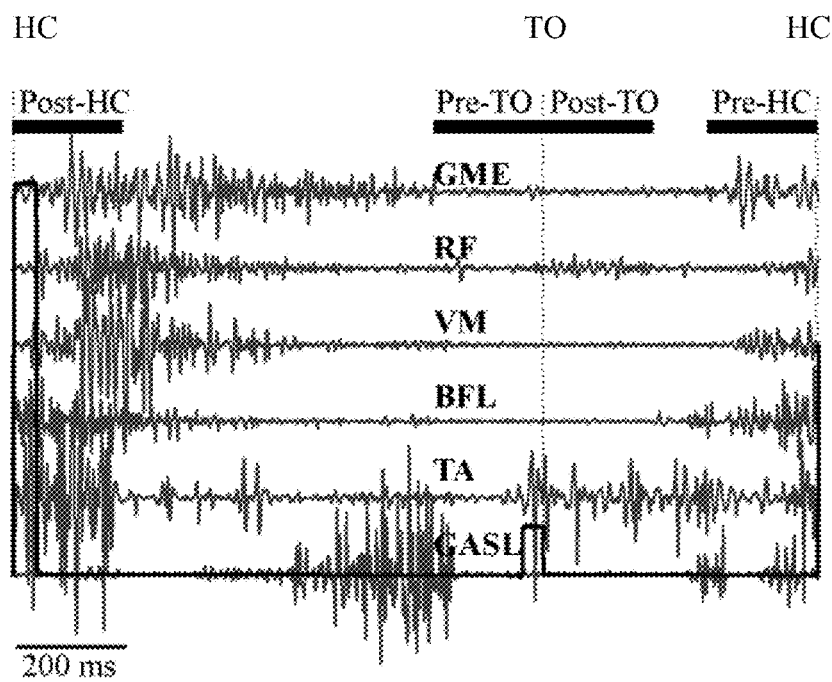
FIG. 6 is a graph showings raw EMG signals and foot-switch pulses in one stride cycle for four defined phase windows aligned with heel contact (HC) and toe-off (TO)

To test phase-dependent PR design concepts, four phase windows aligned with two gait events: heel-contact (HC) and toe-off (TO), were defined (FIG. 6). Specifically, they were defined as the time window (1) immediately after HC (Post- HC), (2) prior to TO (Pre-TO), (3) post toe-off (Post-TO), and (4) prior to the next HC (Pre-HC).

One classifier was built for each phase window. The phase detection module detected the gait events and switched on the associated classifier. At least one decision could be made in every gait phase window. The duration of each phase window was defined as 200 ms, in which the EMG signals were assumed to be quasi-stationary. Data overlapping was observed in the Post-TO and Pre-HC phases for the tasks of level ground walking and descending stairs with relatively short gait cycle duration. Specifically, for the level ground walking, two able-bodied subjects with fast cadence showed an average of 38 ms and 4 ms of data overlapping, separately; for the task of descending stairs, four able-bodied subjects had an average data overlapping ranging from 21 ms to 41 ms between the two phases. To test the hypothesis, the classification accuracy when using the phase-dependent PR system was compared to that when using PR that was composed of one classifier trained by EMG data from the entire stride cycle.

2. EMG Pattern Recognition

Raw EMG data were high-pass filtered with a 25-Hz cutoff frequency to remove motion artifacts. At least ten stride cycles were selected for each task mode. For example, the stride cycles in the turning task were segmented starting at the HC before turning and ending at the next HC with changed foot orientation. For the task of stair descent, although the toes touched the staircase before the heel for able-bodied subjects, the cycles were picked based on the timing of HC. For the phase-dependent PR system, the EMG data of four defined phases were further sampled within each stride cycle.

As previously mentioned, the accuracy of mode recognition and the time-response of the EMG PR algorithm determine its feasibility for prosthesis control. In this test, a simple Linear Discriminant Analysis (LDA)-based classifier was employed, although a more complex and powerful classifier could have been applied.

LDA was reported (1) as having comparable classification performance to more complex types such as Gaussian mixed model (GMM), multilayer perceptron network (MLP), hidden Markov model (HMM), artificial neural network, and fuzzy logic classifier (K. Englehart and B. Hudgins, "A robust, real-time control scheme for multifunction myoelectric control," *IEEE Trans Biomed Eng, vol.* 50, pp. 848-54, 2003; K. Englehart, B. Hudgins, P. A. Parker, and M. Stevenson, "Classification of the myoelectric signal using time-frequency based representations," *Med Eng Phys, vol.* 21, pp. 431-8, 1999; and L. J. Hargrove, K. Englehart, and B. Hudgins, "A comparison of surface and intramuscular myoelectric signal classification," *IEEE Trans Biomed Eng, vol.* 54, pp. 847-53, 2007; Y. Huang, K. B. Englehart, B. Hudgins, and A. D. Chan, "A Gaussian mixture model based classification scheme for myoelectric control of powered upper limb prostheses," *IEEE Trans Biomed Eng, vol.* 52, pp. 1801-11, 2005), and (2) as being computationally efficient for real-time EMG-PR based prosthesis control. The LDA-based EMG pattern recognition algorithm can be found in (H. Huang, P. Zhou, G. Li, and T. A. Kuiken, "An analysis of EMG electrode configuration for targeted muscle reinnervation based neural machine interface," *IEEE Trans Neural Syst Rehabil Eng, vol.* 16, pp. 37-45, 2008), which is incorporated herein by reference.

EMG data were separated into the training set and the testing set. In each phase, EMG features of both training and testing data sets were computed in every analysis window. A feature vector ($\bar{F}$), consisting of features of all applied EMG channels, was formulated as $$\bar{F} = \{\bar{f}_1, \bar{f}_2, \bar{f}_3, \ldots, \bar{f}_N\} \quad (1)$$

where $\bar{f}_n$ denotes the EMG features of channel n, and N denotes the total number of applied EMG channels.

Next, $\bar{F}$ vectors calculated from the training data were used to train the LDA classifier. All the $\bar{F}$ vectors from the testing data were used to test the classifier. Due to the relatively small sample size, leave-one-out cross-validation (LOOCV) was used in each phase for more precise estimation of the classification error. In the LOOCV procedure, data in one gait cycle of each movement mode was applied as the testing data; EMG signals in the remaining cycles were used as training data. This procedure was repeated so that each cycle in all recorded gait cycles was used once as the testing data. To quantify the performance of the classifier, the overall classification error (CE) was calculated by (2) following the LOOCV routine.

$$CE = \frac{\text{Number of Misclassified Testing Data}}{\text{Total Number of Applied Testing Data}} \times 100\%. \quad (2)$$

The overall classification accuracy (CA) was defined as 100%-CE. Additionally, the confusion matrix (C) listing the test results between the targeted classes and the estimated task classes was computed.

$$C = \begin{bmatrix} a_{11} & a_{12} & .. & a_{17} \\ .. & a_{22} & .. & .. \\ .. & .. & .. & .. \\ a_{71} & .. & .. & a_{77} \end{bmatrix}_{7 \times 7}, \quad (3)$$

where the element $$a_{ij} = \frac{\text{Number of Testing Data in Class } i \text{ Estimated as Class } j}{\text{Total Number of Testing Data in Targeted Class } i} \times 100\%. \quad (4)$$

Therefore, the diagonal of the confusion matrix, $a_{ii}$, is the classification accuracy of task class i. Other elements in the matrix indicate the misclassification of EMG patterns between the targeted class i and the estimated class j ($i \neq j$). Note that in the able-bodied subjects' test the averaged classification accuracy over task modes was slightly different from the overall classification accuracy because the number of sampled gait cycles between task modes had a small difference.

3. Study of EMG Features, Length of Analysis Window, and Size of Window Overlap

In order to develop a robust, real-time EMG pattern recognition algorithm, we studied how the classification error (CE) was influenced by the three variables of the classifier: EMG features, length of analysis window, and analysis window increment size. Only the EMG data recorded from the able-bodied subjects were used.

EMG Features:

EMG features, including auto-regression coefficients, time domain features, frequency domain features, and time-frequency domain features, have been used in EMG pattern recognition for upper-limb prosthesis control. Here, we selected the auto-regression and time domain features because their computation does not require signal transformation and therefore satisfies the requirement of fast time-response: (1) Four time domain features (TD) (the mean absolute value, the number of zero-crossings, the waveform length, and the number of slope sign changes), (2) the features with 3-order auto-regression coefficients and the root mean square of a signal (AR), and (3) the features combining TD and 3-order auto-regression coefficients (TDAR) were studied.

Length of the Analysis Window:

The length of analysis window for the EMG feature extraction was determined by the property of the signal. EMG was modeled as a wide-sense Gaussian random process. A short analysis window may elicit a large statistical variance of calculated features. The length of analysis window should not exceed 200 ms, within which the contents of EMG signals were assumed to have small variation. Therefore, the classification errors resulting from different window lengths ranging from 50 ms to 150 ms were compared.

Analysis Window Increment Size:

In addition to the high classification accuracy, fast time-response is desired for real-time classification. A scheme using overlapping analysis windows was applied in order to generate faster decision updates. The smaller the increment of overlapped window, the faster the classification decision can be made.

Analysis of covariance (ANCOVA) was applied to statistically study the effects of EMG features (category variable) and analysis window length (covariate) on classification error. Since the size of the window increment was limited by the analysis window length, the window increment size was studied using one-way analysis of variance (ANOVA) with a fixed window length and feature set.

4. Comparing Classification Error Using Different Amounts of Neuromuscular Control Content.

First, the amount of neuromuscular control content was manipulated by selecting a different subset of EMG channels recorded from the able-bodied subjects. For example, to simulate a transfemoral amputee, the EMG channels measured from below-knee muscles were removed from the system input. The purpose of comparing the classification performance using different combinations of EMG electrodes was two-fold: (1) to identify the importance of neuromuscular control information from different muscle groups for accurate classification, and (2) to quantify the robustness of the designed system with different amounts of neural control contents. Four combinations of EMG channels were studied in eight able-bodied subjects as listed in Table 1.

TABLE 1

| | Muscles | | | |
|---|---|---|---|---|
| | Pelvis Segment GMA, GME | Thigh Segment SAR, RF, VL, VM, GRA, BFL, SEM, BFS | Calf Segment TA, PL, GASL, GASM, SOL | Foot Segment EDB |
| 1 (16 Channels) | Included | Included | Included | Included |
| 2 (10 Channels) | Included | Included | — | — |
| 3 (8 Channels) | — | Included | — | — |
| 4 (6 Channels) | — | — | Included | Included |

Combination 1 included all recorded EMG channels; combination 2 contained EMG channels placed above the knee joint; combination 3 incorporated EMG signals recorded from muscles in the thigh only; and combination 4 was composed of EMG signals from muscles in the calf and foot.

To further evaluate the phase-dependent design for lower-limb prosthesis control, a pilot investigation was conducted on the amount of neural control information in the EMG signals recorded from the residual limb of the TF amputee. The classification error derived when using all recorded EMG signals from the hip and residual limb was compared to the error derived when using nine channels of EMG signals recorded from the residual limb only.

D. Results

Figure 7:
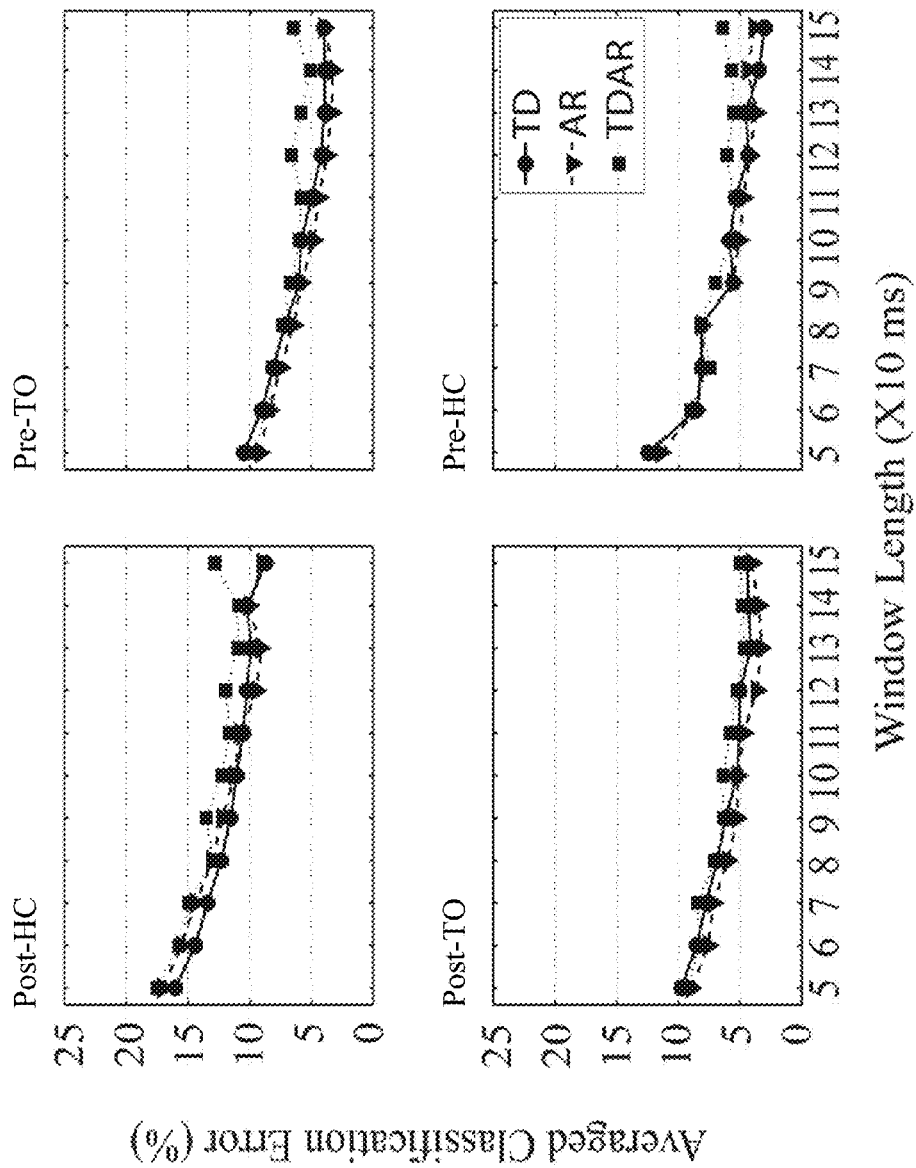
FIG. 7 is a series of graphs illustrating the influence of EMG features and length of the windows on classification error.

1. Effects of EMG Features, Length of the Window, and Size of Window Overlap on Classifier Performance FIG. 7 illustrates the influence of analysis window length and EMG features on the classification error over eight subjects in each defined gait phase when all sixteen EMG channels were applied and the window increment size was set to 30 ms. The average error over eight able-bodied subjects and all applied features dropped 5.0%-7.1% in all four phases when the applied window length increased from 50 ms to 120 ms and remained relatively constant from 120 ms to 150 ms.

Statistically, the analysis window length significantly influenced the classification error ($P<0.05$) in all studied phases; the influence of feature set reached a significant level ($P<0.05$) only in the Pre-TO phase. Additionally, in the Pre-TO phase, each pair of three studied EMG feature sets was compared by the Bonferroni post-hoc test; TDAR features produced significantly higher error than the AR feature set ($P=0.011$) and no significant difference was observed for the other two pairs.

To demonstrate the influence of window increment size on the classifier's performance, the window length was fixed at 140 ms and the EMG features to TD and then studied window increments from 10 ms to 60 ms.

Figure 8:
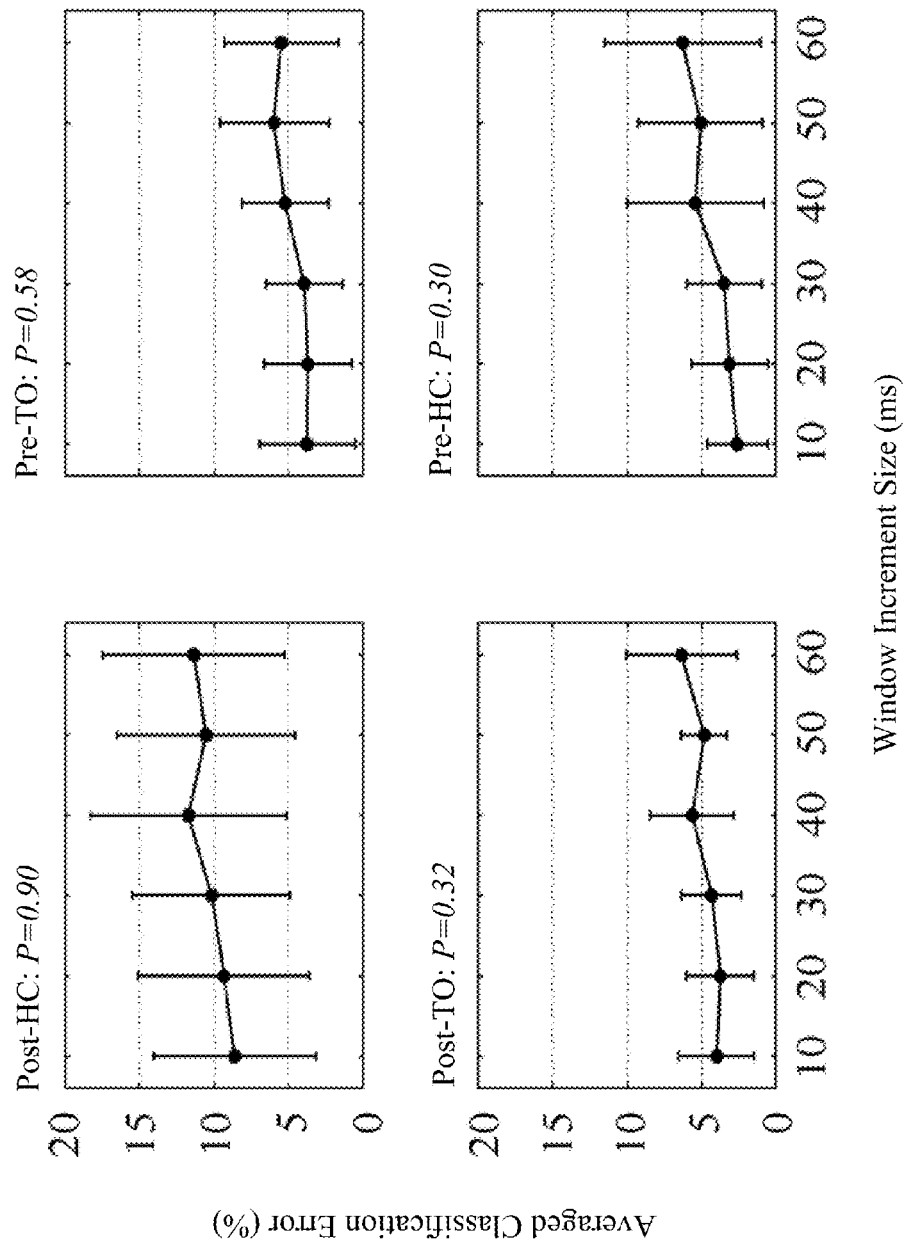
FIG. 8 is a series of graphs illustrating the influence of window increment size on classification error.

FIG. 8 is a series of graphs illustrating the influence of window increment size on classification error, where the classification error averaged over eight subjects is shown in each defined gait phase and the 140-ms analysis window and TD EMG features were applied and the P-values are derived from a one-way ANOVA are presented above each phase. FIG. 8 demonstrates that a smaller window increment provided slightly lower error in the four studied phases. However, this difference was not statistically significant based on the P-value of one-way ANOVA (FIG. 8).

E. Comparison of Classification Error Using Phase-Dependent PR and Full-Stride PR Table 2 demonstrates the average classification errors over eight able-bodied subjects as a result of using the phase-dependent PR and the full-stride PR.

TABLE 2

| | Phase-Dependent PR System | | | | Full-Stride PR System |
|---|---|---|---|---|---|
| | Post-HC | Pre-TO | Post-TO | Pre-HC | |
| Average Classification Error (%) | 10.2 ± 5.3 | 3.9 ± 2.6 | 4.3 ± 2.1 | 3.5 ± 2.5 | 33.7 ± 7.6 |

The following were used: TD features, sixteen EMG channels, 140 ms windows, and 30 ms window increments. Significantly lower error was observed when the designed PR system was composed of the classifiers corresponding to short gait phase windows.

F. Classification Error Using Different Neuromuscular Control Information

Figure 9:
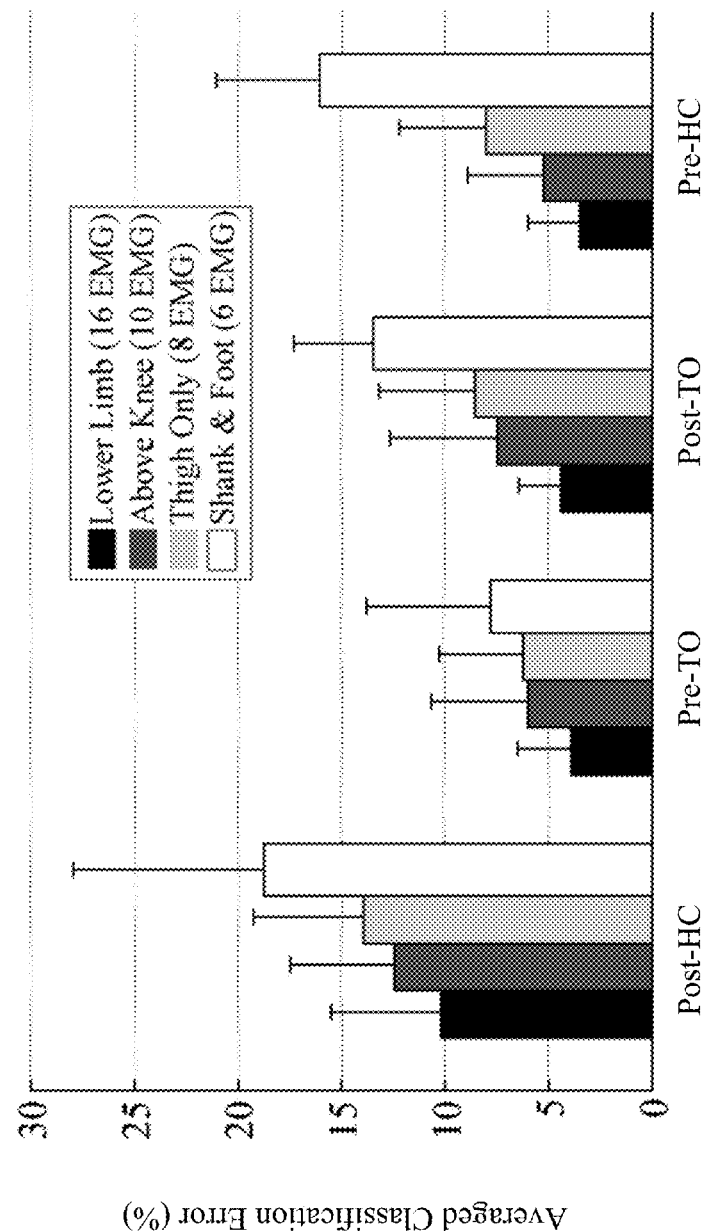
FIG. 9 is a bar chart comparing classification error averaged over eight able-bodied subjects using different amounts of neuromuscular control information.

FIG. 9 is a bar chart comparing classification error averaged over eight able-bodied subjects using different amounts of neuromuscular control information in which Combination 1 (black bars) shows the classification error found using all recorded sixteen EMG channels, Combination 2 (dark gray bar) shows the error found using 10 EMG channels above the knee, Combination 3 (light gray bars) shows the error found using EMG of thigh muscles only, and Combination 4 (white bars) shows the error found using EMG from muscles in shank and foot. FIG. 9 demonstrates the classification errors averaged over the eight able-bodied subjects when the different combinations of EMG signals were used as the input to the designed PR system.

Impressively, when the input EMG signals were from muscles in the hip and thigh (combination 2), the classification error achieved was 12.4±5.0%, 6.0±4.7%, 7.5±5.1%, and 5.2±3.7% in the four studied phase windows (dark gray bars in FIG. 9). Adding more EMG signals from distal muscles further reduced the classification error by 1.8-3.0% (black bars in FIG. 9), and removing two gluteal muscles increased the error by 0.2-2.8% (light gray bars in FIG. 9); however, none of these changes achieved statistical significance ($P>0.05$, one-way ANOVA). Finally, among all studied EMG signal combinations, EMG signals from the shank and foot segments produced the highest classification errors (white bars in FIG. 9).

Figure 10:
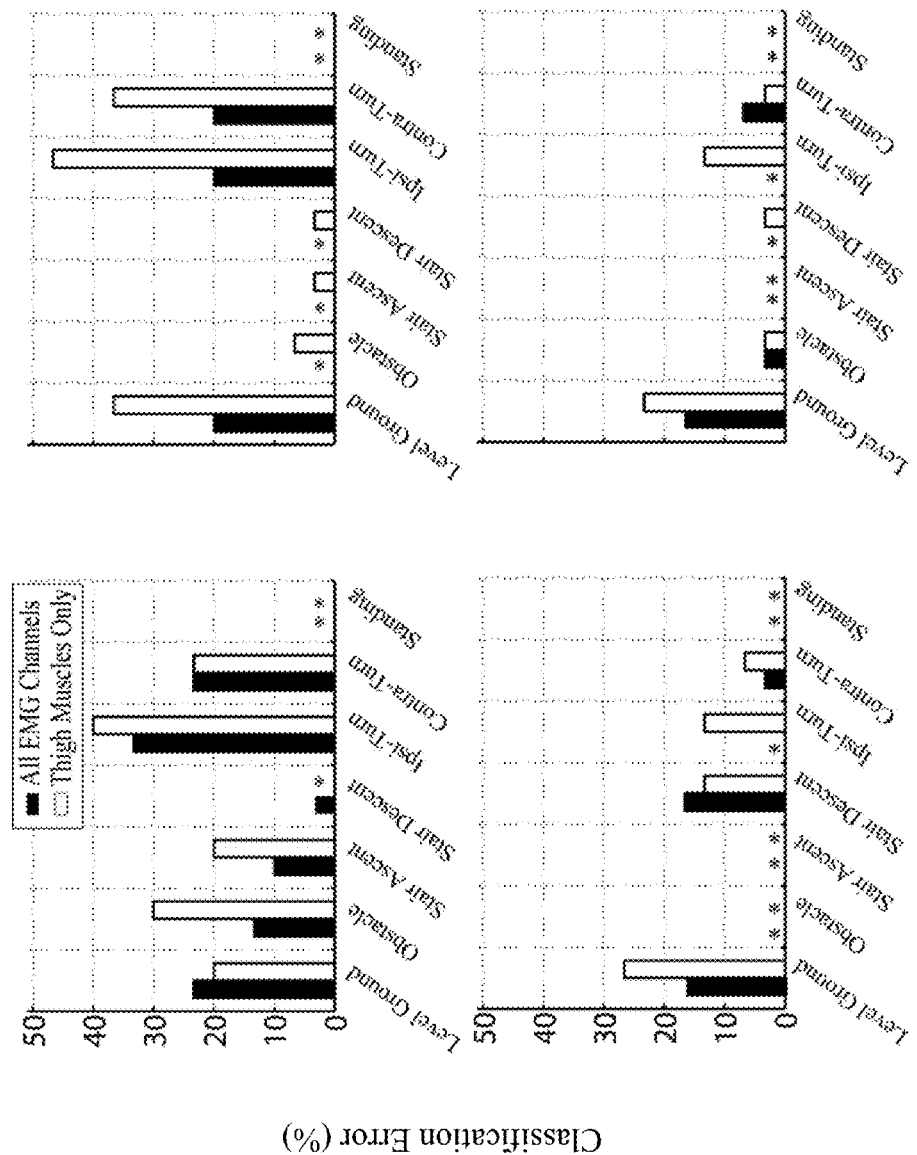
FIG. 10 is a series of bar charts comparing the classification error of each task mode for data recorded from the subject with a transfemoral amputation.

FIG. 10 is a series of bar charts comparing the classification error of each task mode for data recorded from the subject with a transfemoral amputation in which the black bars show the classification error of each task found using all 11 channels of EMG and the white bars show the classification error of each task found using EMG signals in the residual limb only (9 channels).

FIG. 10 demonstrates the error in identifying each individual task as the result of using the data collected from the subject with a TF amputation. When using all EMG signals of gluteal and thigh muscles (black bars in FIG. 10), the overall classification error (CE) was 15.2%, 8.6%, 5.2%, and 3.8% for the four studied phases. When using EMG signals of muscles in the residual limb only, the overall error was 19.0%, 19.0%, 8.6%, and 6.7% for the four phases, respectively.

G. Phase-Dependent Classification Error

Figure 11:
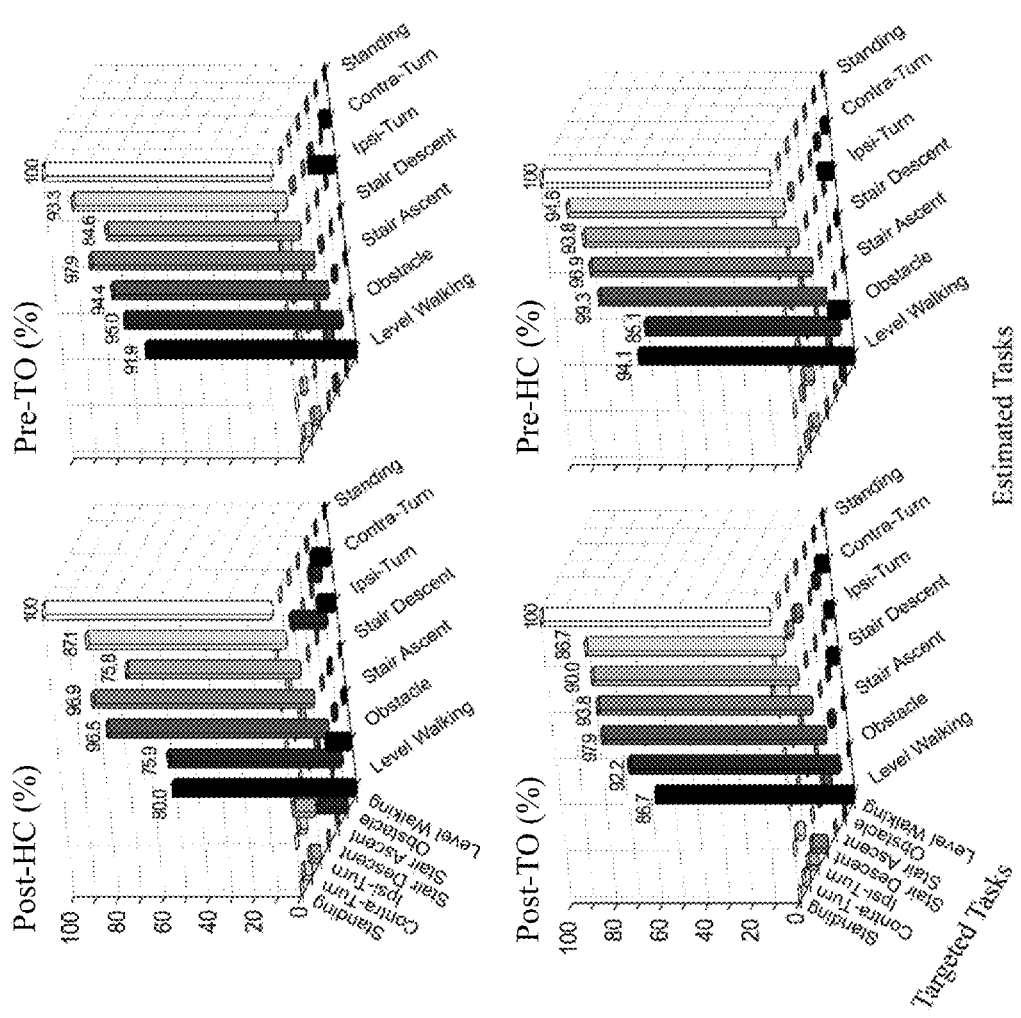
FIG. 11 is a series of bar charts of the confusion matrix for mode classification averaged over eight able-bodied subjects in each phase using EMG from 10 muscles above the knee.

FIGS. 9 and 10 also illustrate that the classification error was phase-dependent. As a result of using the EMG channels above the knee (combination 2), TD features, 140 ms analysis windows, and 30 ms window increments, the confusion matrices averaged over eight able-bodied subjects in four gait phases are shown in FIG. 11. FIG. 11 is a series of bar charts of the confusion matrix for mode classification averaged over eight able-bodied subjects in each phase using EMG from 10 muscles above the knee in which TD features, 140-ms window length, and 30 ms window increments were used, and at the interception of the estimated task j and the targeted task i, a bar is demonstrated, and its height maps the value of element $a_{ij}$ as (4) in the confusion matrix and the diagonal values of the matrix, representing the average classification accuracy rate for individual tasks ($a_{ii}$), are shown above the diagonal bars;

Each element ($a_{ij}$) in the matrix was presented by a bar, the height of which mapped the value of $a_{ij}$. The numbers demonstrated above the diagonal elements ($a_{ii}$) were the averaged classification accuracies for identifying individual tasks.

The lowest classification accuracy rates occurred in the Post-HC phase among tasks of level-ground walking, stepping over an obstacle, and turning. In the other three phases, the accuracies for classifying these movement classes were improved. The tasks of ascending and descending stairs were the most robust locomotion modes to be recognized in all studied phases; the average accuracy to classify these two modes ranged from 93.8% to 99.3%. None of the locomotion modes was confused with the task of standing still. A similar result was also observed for the TF amputee when the EMG signals from his hip and residual limb were applied (black bars in FIG. 10).

These examples demonstrate that the designed phase-dependent EMG PR system was able to accurately recognize seven task modes when sufficient neural control information was present in the input EMG signals, while applying PR to an entire stride could not provide reliable classification with the time-varying EMG input. This supports the teaching of the invention that the non-stationary EMG recorded during locomotion could be modeled as stationary within a short time window.

A notable result is the similar classification error between using EMG combination 2 (Table 1) recorded from the able-bodied subjects (dark gray bars in FIG. 9) and using EMG signals of the amputee subject (black bars in FIG. 10). For both cases, the input EMG signals were recorded from the gluteal muscles and thigh muscles only. This result suggests that sufficient neural control information for accurate classification of various locomotion modes can be extracted from EMG signals recorded from muscles above the knee in able-bodied subjects and possibly individuals with long TF amputations.

Although the participating amputee subject has had a TF amputation for more than 30 years, the muscles in his residual limb still modulated with consistent activation patterns. The amputee's EMG patterns did not necessarily follow the pattern in able-bodied subjects; however, since EMG pattern recognition algorithms adapt to each individual, and the designed phased-dependent EMG PR strategy was able to provide relatively high classification accuracy with the amputee subject as well.

Removing the EMG signals from the hip muscles slightly increased the classification error for the able-bodied subjects (light gray bars in FIG. 9), while for the subject with a TF amputation, the hip muscles were more important for improving the mode identification accuracy during stance phase (Post-HC and Pre-TO phases in FIG. 10). This may be because the hip muscles become more important to stabilize the lower limb during walking for amputee patients. Although there is some difficulty in recording the EMG signals of hip muscles using a prosthetic socket.

Adding the electrodes below the knee represents data that could possibly be made available with targeted muscle reinnervation. The increase in accuracy was modest in the able bodied subjects with this control scheme. This suggests TMR may not be needed with this control scheme for long transfemoral amputees. However, TMR may improve pattern classification accuracy if hip muscle EMG is not used in the long transfemoral amputee and it is likely that TMR can be useful for patients with short TF or higher levels of amputation.

When the recordable neuromuscular control information is highly limited, TMR could allow neural control data to be accessible for the lower amputated leg muscles and, therefore, augment mode selection subconsciously if the system is made robust.

In addition, TMR might be feasible for other EMG-based prosthesis control paradigms. For example, one can restore a dorsiflexion signal from a common peroneal nerve transfer or a plantar flexion signal from a tibial nerve transfer. These signals could be used consciously for mode selection: a strong voluntary dorsiflexion signal may be used to put the prosthesis into a stair climbing mode and a strong plantar flexion signal may be used to put the leg into a stair descending mode. Finally, TMR may be of value for multi-articular control of powered leg prostheses.

The mode selection error rates were higher when recording only from muscles below the knee (as with transtibial amputation) with these tasks. Knee and hip EMG signals clearly added more information to identify the subject's mode of movement.

The accuracy in recognizing locomotion modes also depends on the gait phase and the investigated tasks. The Post-HC phase is the very beginning of the transition between the level-ground walking task and other tasks; the difference in EMG patterns among the tasks of level-ground walking, stepping over an obstacle, and turning was subtle so that the classifier could not as clearly separate these locomotion modes (FIG. 11 for the able-bodied subjects and FIG. 10 for the amputee subject).

An accurate decision before toe-off and heel contact is important for assuring safety, because the controller could decide the motion of the prosthetic knee before the execution of the swing and the next weight acceptance. Surprisingly, the high risk activities of stair ascent and descent were the most easily identified among the studied locomotion tasks; this is perhaps because these two tasks had significantly different kinematics and kinetics and involved more voluntary drive (attention) from the user.

The following variable designs can be used to build a robust, real-time EMG pattern classifier for identifying user locomotion modes:

1. TD and AR features are computationally efficient and provide similar classification accuracy compared to TDAR features; TD and AR features are preferred;
2. Analysis windows lengths greater than 120 ms are desirable (FIG. 9). This result is consistent with the outcomes of several previous studies, but is opposite to the result reported by Hudgins et al. (See B. Hudgins, P. Parker, and R. N. Scott, "A new strategy for multifunction myoelectric control," *IEEE Trans Biomed Eng*, vol. 40, pp. 82-94, 1993). Hudgins et al. reasoned that the shorter analysis window could better capture the features of deterministic signal components, which were found in the studied transient EMG signals and were considered to be motion artifacts. Here, the slow wave and motion artifacts were filtered out, resulting in a different outcome than their study.
3. A small increment permits fast decision updates without influencing the classification error. Nevertheless, the minimum increment size must be limited by the processing delay, which consists of the time required to compute the feature vector and discriminate the data and depends on the applied hardware system.

One promising technique called multi-sensor fusion (See D. Hall and J. Llinas, "An introduction to multisensor data fusion," *Proceedings of IEEE*, vol. 85, pp. 6-23, 1997; and H. Huang, S. L. Wolf, and J. He, "Recent developments in biofeedback for neuromotor rehabilitation," *J Neuroengineering Rehabil*, vol. 3, pp. 11, 2006, which are incorporated herein by reference), could improve the classification accuracy by basing class decisions not only on EMG data but also on peripheral sensing data, such as ground reaction forces and joint kinematics monitored from the prosthesis.

The idea of multisensor fusion is to enhance machine perception and pattern recognition accuracy by sensing multiple sources of data rather than a single source. Hence, the active prosthetic controller acts as a secondary brain that makes accurate control decisions by integrating the voluntary drive recorded from EMG signals and the peripheral feedback, simulating proprioception.

In addition, the control safety could be further reinforced by using the already existing safety mechanisms achieved in current leg systems. In further embodiments of the invention, control systems that fuse EMG neural control data with this type of intrinsic prosthesis data can be provided.

The constant length of the phase window (200 ms) appears to be inappropriate for a task with a short stride cycle or for a person with fast cadence. Since muscle activity is directly related to the dynamic control of each gait phase, the classifiers may need to be built corresponding to clinically and functionally defined phases. Various embodiments of the present invention provide for a use of measured EMG data that can subsequently be used for neural prosthesis control.

All references, including publications, patent applications, and patents, cited herein are hereby incorporated by reference to the same extent as if each reference were individually and specifically indicated to be incorporated by reference and were set forth in its entirety herein.

The system or systems may be implemented on any form of computer or computers, and can include functional programs, codes, and code segments. Any of the computers may comprise a processor, a memory for storing program data and executing it, a permanent storage, a communications port for handling communications with external devices, and user interface devices. When software modules are involved, these software modules may be stored as program instructions or computer readable codes executable on the processor on a computer-readable media such as read-only memory (ROM), random-access memory (RAM), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion. This media can be read by the computer, stored in the memory, and executed by the processor.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical".

The use of the terms "a" and "an" and "the" and similar referents in the context of describing the invention (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein can be performed in any suitable order unless otherwise indicated herein or otherwise clearly contradicted by context.

Numerous modifications and adaptations will be readily apparent to those skilled in this art without departing from the spirit and scope of the present invention.

What is claimed is:

1. A lower-limb prosthesis operating assembly, comprising:
   (a) one or more prosthesis sensors, each one for measuring one or more prosthesis characteristics and for providing signals corresponding to values of the prosthesis characteristics at a prosthesis sensor output;
   (b) a plurality of EMG sensors for receiving non-stationary EMG signals;
   (c) a processor comprising:
      (i) one or more processor inputs, configured to be connected to one or more of (1) a prosthesis sensor output, for receiving one or more prosthesis characteristic value signals, and (2) an EMG sensor, for receiving EMG signals;
      (ii) a gait phase means for determining a gait phase, a gait phase information relating to the gait phase, based on the prosthesis characteristic values; and
      (iii) a means for determining a locomotion mode based on the EMG signals received during a phase window of a gait cycle and the gait phase information; and
   (d) a locomotion mode output that provides a signal corresponding to the determined locomotion mode at the determined gait phase to a prosthesis controller input.

2. The assembly according to claim 1, the EMG sensor signals are digitized prior to receipt by the one or more inputs of the processor.

3. The assembly according to claim 1, further comprising: a memory for storing the determined locomotion mode.

4. The assembly according to claim 1, further comprising: a memory for storing the determined gait phase information.

5. The assembly according to claim 1, wherein the gait phase means comprises a gait phase algorithm comprising program instructions that execute on the processor.

6. The assembly according to claim 1, wherein the means for determining a locomotion mode comprises a locomotion mode algorithm comprising program instructions that execute on the processor.

7. The assembly according to claim 1, wherein the locomotion mode comprises level walking, obstacle, stair ascent, stair descent, ipsi-turn, contra-turn, and standing.

8. The assembly according to claim 1, wherein the gait phases comprise a post-heel-contact phase, a pre-toe-off phase, a post-toe-off phase, and a pre-heel-contact phase.

9. The assembly according to claim 1, wherein the phase window is between about 120 ms and 200 ms in duration.

10. The assembly according to claim 1, wherein the prosthesis sensors include a heel sensor and a toe sensor and the gait phase is determined based on prosthesis characteristic value signals of these sensors.

11. The assembly according to claim 1, wherein the prosthesis sensors include a three-degree-of-freedom load cell and the gait phase is determined based on the output of this load cell.

12. The assembly according to claim 1, wherein the processor is a floating point processor.

13. The assembly according to claim 1, wherein the prosthesis characteristics are selected from the group consisting of position, angle, velocity, acceleration, torque, and linear vector forces.

14. The assembly according to claim 1, wherein the means for determining the locomotion mode is configured as a pattern recognition algorithm.

15. The assembly according to claim 14, wherein the pattern recognition algorithm is a linear discriminant analysis-based classifier.

16. The assembly according to claim 14, wherein a classifier for the pattern recognition algorithm is selected from the group consisting of: a Gaussian mixed model, a multilayer perceptron network, a hidden Markov model, an artificial neural network, and a fuzzy logic classifier.

17. The assembly according to claim 1, wherein the EMG sensors are placed for measuring a plurality of signals from muscles selected from the group consisting of: gluteus maximus; gluteus medius; sartorius; rectus femoris; vastus lateralis; vastus medialis; gracilis; biceps femoris long head; semitendinosus; biceps femoris short head; tibialis anterior; peroneus longus; gastrocnemius lateral head; gastrocnemius medial head; soleus; and extensor digitorum brevis.

18. The assembly according to claim 1, wherein the EMG sensors are polarizable stainless steel domes embedded into a socket or liner of a prosthesis.

19. The assembly according to claim 1, further comprising a communication module for communication between the processor and a computer output information acquired by the assembly or input information utilized by the assembly.

20. The assembly according to claim 1, wherein the EMG sensors are affixed to a portion of the assembly.

21. The assembly according to claim 1, wherein the phase window is of a shorter duration than an entire stride of the assembly.

22. The assembly according to claim 1, wherein the means for determining a locomotion mode is based on the EMG signals received during a phase window of the immediately prior gait cycle.

* * * * *